(12) United States Patent
Nicol et al.

(10) Patent No.: US 9,738,930 B2
(45) Date of Patent: Aug. 22, 2017

(54) PAIRED END BEAD AMPLIFICATION AND HIGH THROUGHPUT SEQUENCING

(75) Inventors: Robert Nicol, Cambridge, MA (US); Niall J. Lennon, Tullow (IE)

(73) Assignee: The Broad Institute, Inc., Cambridge, MA (US)

(*) Notice: Subject to any disclaimer, the term of this patent is extended or adjusted under 35 U.S.C. 154(b) by 424 days.

(21) Appl. No.: 13/981,412

(22) PCT Filed: Jan. 27, 2012

(86) PCT No.: PCT/US2012/022913
§ 371 (c)(1),
(2), (4) Date: Oct. 10, 2013

(87) PCT Pub. No.: WO2012/103442
PCT Pub. Date: Aug. 2, 2012

(65) Prior Publication Data
US 2014/0031241 A1    Jan. 30, 2014

Related U.S. Application Data

(60) Provisional application No. 61/437,167, filed on Jan. 28, 2011.

(51) Int. Cl.
*C12Q 1/68* (2006.01)
*C40B 50/14* (2006.01)

(52) U.S. Cl.
CPC ......... *C12Q 1/6874* (2013.01); *C12Q 1/6806* (2013.01); *C12Q 1/6869* (2013.01); *C40B 50/14* (2013.01)

(58) Field of Classification Search
None
See application file for complete search history.

(56) References Cited

U.S. PATENT DOCUMENTS

| | | | |
|---|---|---|---|
| 5,639,603 A | 6/1997 | Dower et al. | |
| 5,683,869 A | 11/1997 | Ramsay Shaw et al. | |
| 5,859,231 A | 1/1999 | Shaw et al. | |
| 5,874,259 A | 2/1999 | Szybalski | |
| 6,165,778 A | 12/2000 | Kedar | |
| 6,376,178 B1 | 4/2002 | Shaw et al. | |

(Continued)

FOREIGN PATENT DOCUMENTS

| | | |
|---|---|---|
| JP | 2008-545448 A | 12/2008 |
| WO | WO 2006/084132 A2 | 8/2006 |

OTHER PUBLICATIONS

Adams et al., The genome sequence of *Drosophila melanogaster*. Science. Mar. 24, 2000;287(5461):2185-95.

(Continued)

*Primary Examiner* — Kaijiang Zhang
(74) *Attorney, Agent, or Firm* — Wolf, Greenfield & Sacks, P.C.

(57) ABSTRACT

The present invention is related to genomic nucleotide sequencing. In particular, the invention describes a paired end sequencing method that enables the sequencing of unique read pairs by co-localizing both 5' ends on a single emulsion polymerase chain reaction bead. The method may use a customized forked adaptor primer pair that is compatible with massively parallel sequencing techniques. The compositions and methods disclosed herein contemplate sequencing complex genomes, amplified genomic regions, as well as detecting chromosomal structural rearrangements.

6 Claims, 8 Drawing Sheets

A

B

C

(56) References Cited

U.S. PATENT DOCUMENTS

| | | |
|---|---|---|
| 6,436,635 B1 | 8/2002 | Fu et al. |
| 6,709,861 B2 | 3/2004 | Mead et al. |
| 6,991,903 B2 | 1/2006 | Fu et al. |
| 7,211,414 B2 | 5/2007 | Hardin et al. |
| 7,303,885 B1 | 12/2007 | Brunner et al. |
| 7,627,437 B2 | 12/2009 | Forney et al. |
| 7,833,769 B2 | 11/2010 | Anton et al. |
| 7,964,349 B2 | 6/2011 | Bell et al. |
| 2007/0054311 A1 | 3/2007 | Kamberov et al. |
| 2007/0269870 A1 | 11/2007 | Church et al. |
| 2009/0202984 A1 | 8/2009 | Cantor |
| 2010/0016170 A1 | 1/2010 | Farnet et al. |
| 2010/0055702 A1 | 3/2010 | Battle et al. |
| 2010/0222238 A1 | 9/2010 | Smith et al. |
| 2010/0240101 A1 | 9/2010 | Lieberman et al. |
| 2010/0273219 A1 | 10/2010 | May et al. |
| 2010/0273662 A1 | 10/2010 | Gormley et al. |
| 2014/0228223 A1 | 8/2014 | Gnirke et al. |
| 2014/0243242 A1 | 8/2014 | Nicol et al. |

OTHER PUBLICATIONS

Ansorge et al., Next-generation DNA sequencing techniques. N Biotechnol. Apr. 2009;25(4):195-203. doi: 10.1016/j.nbt.2008.12.009. Epub Feb. 3, 2009. Review.

Bentley et al., Accurate whole human genome sequencing using reversible terminator chemistry. Nature. Nov. 6, 2008;456(7218):53-9. doi: 10.1038/nature07517.

Braslavsky et al., Sequence information can be obtained from single DNA molecules. Proc Natl Acad Sci U S A. Apr. 1, 2003;100(7):3960-4. Epub Mar. 21, 2003.

Brenner et al., Gene expression analysis by massively parallel signature sequencing (MPSS) on microbead arrays. Nat Biotechnol. Jun. 2000;18(6):630-4. Erratum in: Nat Biotechnol Oct. 2000;18(10):1021.

Campbell et al., Identification of somatically acquired rearrangements in cancer using genome-wide massively parallel paired-end sequencing. Nat Genet. Jun. 2008;40(6):722-9. doi: 10.1038/ng.128.

Cloonan et al., Stem cell transcriptome profiling via massive-scale mRNA sequencing. Nat Methods. Jul. 2008;5(7):613-9. doi: 10.1038/nmeth.1223.

Dressman et al., Transforming single DNA molecules into fluorescent magnetic particles for detection and enumeration of genetic variations. Proc Natl Acad Sci U S A. Jul. 22, 2003;100(15):8817-22. Epub Jul. 11, 2003.

Edwards et al., Automated DNA sequencing of the human HPRT locus. Genomics. Apr. 1990;6(4):593-608.

Edwards et al., Closure strategies for random DNA sequencing. Methods: A Companion to Methods in Enzymology. 1991;3:41-7.

Eid et al., Real-time DNA sequencing from single polymerase molecules. Science. Jan. 2, 2009;323(5910):133-8. doi: 10.1126/science.1162986.

Fleischmann et al., Whole-genome random sequencing and assembly of Haemophilus influenzae Rd. Science. Jul. 28, 1995;269(5223):496-512.

Fullwood et al., Next-generation DNA sequencing of paired-end tags (PET) for transcriptome and genome analyses. Genome Res. Apr. 2009;19(4):521-32. doi: 10.1101/gr.074906.107. Review.

Gibbs et al., Evolutionary and biomedical insights from the rhesus macaque genome. Science. Apr. 13, 2007;316(5822):222-34.

Harris et al., Single-molecule DNA sequencing of a viral genome. Science. Apr. 4, 2008;320(5872):106-9. doi: 10.1126/science.1150427.

Ju et al., Four-color DNA sequencing by synthesis using cleavable fluorescent nucleotide reversible terminators. Proc Natl Acad Sci U S A. Dec. 26, 2006;103(52):19635-40. Epub Dec. 14, 2006.

Korbel et al., Paired-end mapping reveals extensive structural variation in the human genome. Science. Oct. 19, 2007;318(5849):420-6. Epub Sep. 27, 2007.

Lundquist et al., Parallel confocal detection of single molecules in real time. Opt Lett. May 1, 2008;33(9):1026-8.

Mardis et al., Next-generation DNA sequencing methods. Annu Rev Genomics Hum Genet. 2008;9:387-402. doi: 10.1146/annurev.genom.9.081307.164359. Review.

Margulies et al., Genome sequencing in microfabricated high-density picolitre reactors. Nature. Sep. 15, 2005;437(7057):376-80. Epub Jul. 31, 2005. Erratum in: Nature. May 4, 2006;441(7089):120.

Porreca et al., Polony DNA sequencing. Curr Protoc Mol Biol. Nov. 2006;Chapter 7:Unit 7.8. doi: 10.1002/0471142727.mb0708s76. Review.

Roach et al., Pairwise end sequencing: a unified approach to genomic mapping and sequencing. Genomics. Mar. 20, 1995;26(2):345-53.

Ronaghi et al., Analyses of secondary structures in DNA by pyrosequencing. Anal Biochem. Feb. 1, 1999;267(1):65-71.

Ronaghi et al., Real-time DNA sequencing using detection of pyrophosphate release. Anal Biochem. Nov. 1, 1996;242(1):84-9.

Shendure et al., Accurate multiplex polony sequencing of an evolved bacterial genome. Science. Sep. 9, 2005;309(5741):1728-32.

Shendure et al., Next-generation DNA sequencing. Nat Biotechnol. Oct. 2008;26(10):1135-45. doi: 10.1038/nbt1486.

Tawfik et al., Man-made cell-like compartments for molecular evolution. Nat Biotechnol. Jul. 1998;16(7):652-6.

Valouev et al., A high-resolution, nucleosome position map of C. elegans reveals a lack of universal sequence-dictated positioning. Genome Res. Jul. 2008;18(7):1051-63. doi: 10.1101/gr.076463.108.

Wheeler et al., The complete genome of an individual by massively parallel DNA sequencing. Nature. Apr. 17, 2008;452(7189):872-6. doi: 10.1038/nature06884.

International Search Report and Written Opinion mailed May 16, 2012 for Application No. PCT/US2012/022913.

Metzker, Sequencing technologies—the next generation. Nat Rev Genet. Jan. 2010;11(1):31-46. Review.

Xu et al., Dual primer emulsion PCR for next-generation DNA sequencing. Biotechniques. May 2010;48(5):409-12. Supplementary Material: Biotechniques. May 2010;48(5): 351-3.

International Preliminary Report on Patentability mailed May 21, 2015 for Application No. PCT/US2012/022913.

Extended European Search Report for European Application No. 12738736.3 mailed Aug. 22, 2016.

[No Author Listed], Applied Biosystems SOLiDTM 4 System Library Preparation Guide, Chapter 3: Mate-Paired Library Preparation (Apr. 2010). 86 pages.

[No Author Listed], Applied Biosystems SOLiD™ 4 System. Library Preparation Guide. Applied Biosystems. Apr. 2010 259 pages.

[No Author Listed], International Human Genorne Sequencing Consortium. Finishing the euchromatic sequence of the human genome. Nature. Oct. 21, 2004;431(7011):931-45.

Anderson, Shotgun DNA sequencing using cloned DNase I-generated fragments. Nucleic Acids Res. Jul. 10, 1981;9(13):3015-27.

Bates et al., Double cos site vectors: simplified cosmid cloning. Gene. Dec. 1983;26(2-3):137-46. PubMed PMID: 6323255.

Butler et al., ALLPATHS: de novo assembly of whole-genome shotgun microreads. Genome Res. May 2008;18(5):810-20. doi: 10.1101/gr.7337908. Epub Mar. 13, 2008.

Church et al., Genomes for all. Sci Am. Jan. 2006;294(1):46-54.

Collins et al., (1987) Construction of a General Human Chromosome Jumping Library, with Application to Cystic Fibrosis, Science 235(4792): 1046-1049.

Collins et al., Directional cloning of DNA fragments at a large distance from an initial probe: a circularization method. Proc Natl Acad Sci U S A. Nov. 1984;81(21):6812-6.

David et al., An improved copycontrol fosmid vector maximizes end-sequencing results. Epicentre Forum, 2006;13(1):17.

Evans et al., High efficiency vectors for cosmid microcloning and genomic analysis. Gene. Jun. 30, 1989;79(1):9-20.

Fedurco et al., BTA, a novel reagent for DNA attachment on glass and efficient generation of solid-phase amplified DNA colonies. Nucleic Acids Res. Feb. 9, 2006;34(3):e22.

(56) References Cited

OTHER PUBLICATIONS

Gnerre et al., High-quality draft assemblies of mammalian genomes from massively parallel sequence data. Proc Natl Acad Sci U S A. Jan. 25, 2011;108(4):1513-8. doi:10.1073/pnas.1017351108. Epub Dec. 27, 2010.

Godiska et al., Linear plasmid vector for cloning of repetitive or unstable sequences in *Escherichia coli*. Nucleic Acids Res. Apr. 2010;38(6):e88. doi: 10.1093/nar/gkpl181. Epub Dec. 29, 2009.

Hall., Advanced sequencing technologies and their wider impact in microbiology. J Exp Biol. May 2007;210(Pt 9):1518-25.

Kim et al., Stable propagation of cosmid sized human DNA inserts in art F factor based vector. Nucleic Acids Res. Mar. 11, 1992;20(5):1083-5.

Levy et al. The diploid genome sequence of an individual human. PLoS Biol. Sep. 4, 2007;5(10):e254. pp. 2113-2144.

Li et al., The sequence and de novo assembly of the giant panda genome. Nature. Jan. 21, 2010;463(7279):311-7. doi:10.1038/nature08696. Epub Dec. 13, 2009.

Li et al., De novo assembly of human genomes with massively parallel short read sequencing. Genome Res. Feb. 2010;20(2):265-72. doi:10.1101/gr.097261.109. Epub Dec. 17, 2009.

Lindblad-Toh et al., Genome sequence, comparative analysis and haplotype structure of the domestic dog. Nature. Dec. 8, 2005;438(7069):803-19.

Lozzio et al., Human chronic myelogenous leukemia cell-line with positive Philadelphia chromosome. Blood. Mar. 1975,45(3):321-34.

MacCallum et al., ALLPATHS 2: small genomes assembled accurately and with high continuity from short paired reads. Genome Biol. 2009;10(10):R103. doi: 10.1186/gb-2009-10-10-r103. Epub Oct. 1, 2009.

McKernan et al. (2009) Sequence and Structural Variation in a Human Genome Uncovered by Short-Read, massively Parallel Ligation Sequencing Using Two-Base Encoding, Genome Research 19: 1527-1541.

Mikkelsen et al., Genome of the marsupial Monodelphis domestica reveals innovation in non-coding sequences. Nature. May 10, 2007;447(7141):167-77.

Nowrousian et al., De novo assembly of a 40 Mb eukaryotic genome from short sequence reads: Sordaria macrospora, a model organism for fungal morphogenesis. PLoS Genet. Apr. 8, 2010;6(4):e1000891. doi:10.1371/journal.pgen.1000891.

Ochman et al., Genetic applications of an inverse polymerase chain reaction. Genetics Nov. 1988;120(3):621-3.

Olsvik et al., Use of automated sequencing of polymerase chain reaction-generated amplicons to identify three types of cholera toxin subunit B in Vibrio cholerae O1 strains. J Clin Microbiol. Jan. 1993;31(1):22-5.

Pemov et al., DNA analysis with multiplex microarray-enhanced PCR. Nucleic Acids Res. Jan. 20, 2005;33(2):e11.

Poustka et al., (1987) Construction and use of Human Chromosome Jumping Libraries from NotI-Digested DNA, Nature 325: 353-355.

Rothberg et al., An integrated semiconductor device enabling non-optical genome sequencing. Nature. Jul. 20, 2011;475(7356):348-52. Supplementary Information, 25 pages. doi: 10.1038/nature10242.

Schuster et al., Complete Khoisan and Bantu genomes from southern Africa. Nature. Feb. 18, 2010;463(7283):943-7. doi:10.1038/nature08795.

Waterston et al., Initial sequencing and comparative analysis of the mouse genome.Nature. Dec. 5, 2002;420(6915):520-62.

Williams et al., Paired-end sequencing of Fosmid libraries by Illumina. Genome Res. Nov. 2012;22(11):2241-9. doi:10.1101/gr.138925.112. Epub Jul. 16, 2012. Supplemental Material Included. 10 Pages.

Zerbino et al., Velvet: algorithms for de novo short read assembly using de Bruijn graphs. Genome Res. May 2008;18(5):821-9. doi: 10.1101/gr.074492.107. Epub Mar. 18, 2008.

Zhang et al., A novel degradation pathway of chloroaniline in *Diaphorobacter* sp. PCA039 entails initial hydroxylation. World J Microbiol Biotechnol. Apr. 2010;26(4):665-73.

A

B

A

B

C

A

Green and Red Laser

B

Green laser alone

C

Red laser alone

PAIRED END BEAD AMPLIFICATION AND HIGH THROUGHPUT SEQUENCING

RELATED APPLICATIONS

This application is a national stage filing under 35 U.S.C. §371 of International Application No. PCT/US2012/022913 filed Jan. 27, 2012, which was published under PCT Article 21(2) in English and which claims the benefit of U.S. provisional Application Ser. No. 61/437,167 filed Jan. 28, 2011, each of which is herein incorporated by reference in its entirety for all purposes.

FIELD OF THE INVENTION

The present invention is related to genomic nucleotide sequencing. In particular, the invention describes a paired end sequencing method that enables the sequencing of unique read pairs by co-localizing both 5' ends on a single emulsion polymerase chain reaction bead. The method may use a customized forked adaptor primer pair that is compatible with massively parallel sequencing techniques. The compositions and methods disclosed herein contemplate sequencing complex genomes, amplified genomic regions, as well as detecting chromosomal structural rearrangements.

BACKGROUND

Recent advances in sequencing technology have rapidly driven down the cost of DNA sequence data and yield an unrivalled resource of genetic information. Individual genomes can be characterized, while genetic variation may be studied in populations and disease. Until recently, the scope of sequencing projects was limited by the cost and throughput of Sanger sequencing. The raw data for the three billion base (3 gigabase (Gb)) human genome sequence was generated over several years for ~$300 million using several hundred capillary sequencers. International Human Genome Sequencing Consortium, "Finishing the euchromatic sequence of the human genome" *Nature* 431:931-945 (2004). More recently, an individual human genome sequence has been determined for ~$10 million by capillary sequencing. Levy et al., "The diploid genome sequence of an individual human" *PLoS Biol.* 5:e254 (2007). Several new approaches at varying stages of development aim to increase sequencing throughput and reduce cost. Margulies et al., "Genome sequencing in microfabricated high-density picoliter reactors" *Nature* 437:376-380 (2005); Shendure et al., "Accurate multiplex polony sequencing of an evolved bacterial genome" *Science* 309:1728-1732 (2005); Harris et al., "Single-molecule DNA sequencing of a viral genome" *Science* 320:106-109 (2008); and Lundquist et al., "Parallel confocal detection of single molecules in real time" *Opt. Lett.* 33:1026-1028 (2008). These techniques increase parallelization markedly by imaging many DNA molecules simultaneously. One instrument run produces typically thousands or millions of sequences that are shorter than capillary reads. Another human genome sequence was recently determined using one of these approaches. Wheeler et al., "The complete genome of an individual by massively parallel DNA sequencing" *Nature* 452:872-876 (2008). Moreover, an international consortium is currently in the process of determining the genome sequence of at least a thousand different human individuals (1000genomes.org/page.php?page=home). These human genome sequences are typically based on the pre-existing human reference sequence and are not assembled de novo (i.e., without prior knowledge of the reference sequence)

However, further improvements are necessary to improve the efficiency of these massively parallel sequencing systems to enable routine sequencing and assembly of complex genomes de novo (i.e., without a pre-existing reference sequence). Essentially all methods for assembling genomes de novo require pairs of sequencing reads that have an a priori defined orientation and spacing in the underlying genome. Short-distance read pairs (i.e., for example 25-500 bps) are usually employed, even to provide information regarding long-range contiguity of genome assemblies. Using such short-distance read pairs, genome assemblies remain highly fragmented. Approaches that improve amplification yield and sequencing efficiency of massively-parallel sequencers using short-distance read pairs would greatly improve the quality of genome assemblies.

The ability to produce sequence reads from distal ends of a single DNA fragment (paired-end sequencing) is extremely useful for many down stream analyses. Currently there are no sequencing by polymerase synthesis commercially available methods for effective paired-end sequencing from beads on any of the established bead-based sequencing technologies (AB Solid, Roche/454 and now Ion Torrent).

SUMMARY OF THE INVENTION

The present invention is related to genomic nucleotide sequencing. In particular, the invention describes a paired end sequencing method that enables the sequencing of unique read pairs by co-localizing both 5' ends on a single emulsion polymerase chain reaction bead. The method may use a customized forked adaptor primer pair that is compatible with massively parallel sequencing techniques. The compositions and methods disclosed herein contemplate sequencing complex genomes, amplified genomic regions, as well as detecting chromosomal structural rearrangements.

In one embodiment, the present invention contemplates a composition comprising a solid support attached to a first emulsion primer and a second emulsion primer, wherein said first emulsion primer is ligated to a first nucleic acid sequence comprising a first portion of a genomic DNA sequence and said second emulsion primer is ligated to a second nucleic acid comprising a second portion of said genomic DNA sequence. In one embodiment, the first and second emulsion primers are attached the solid support at the 5' end. In one embodiment, the solid support is a bead. In one embodiment, the composition further comprises a first high throughput sequencing primer hybridized to said first nucleic acid sequence. In one embodiment, the composition further comprises a second high throughput sequencing primer hybridized to said second nucleic acid sequence.

In one embodiment, the present invention contemplates a composition comprising a forked end adapter comprising a duplex DNA sequence, wherein said duplex DNA sequence comprises a first nucleic acid sequence ligated to a primer sequence and a second nucleic acid sequence ligated to a primer binding sequence. In one embodiment, the primer sequence is an emulsion primer sequence. In one embodiment, the second primer binding sequence is an emulsion primer binding sequence.

In one embodiment, the present invention contemplates a composition comprising a forked end adapter comprising a duplex DNA sequence, wherein said duplex DNA sequence comprises a first nucleic acid sequence ligated to a primer sequence and a second nucleic acid sequence ligated to a barcode sequence. In one embodiment, the primer sequence is an emulsion primer sequence.

In one embodiment, the present invention contemplates a composition comprising a ligated forked adapter pair, wherein said adapter pair comprises a first duplex DNA sequence ligated to a second duplex DNA sequence, said first duplex DNA sequence comprising a first nucleic acid sequence ligated to a first primer sequence and a second nucleic acid sequence ligated to a first primer binding sequence, and said second duplex DNA sequence ligated to a third nucleic acid sequence ligated to a second primer sequence and a fourth nucleic acid sequence ligated to a second primer binding sequence. In one embodiment, the first primer sequence is an emulsion primer sequence. In one embodiment, the first primer binding sequence is an emulsion primer binding sequence. In one embodiment, the second primer sequence is an emulsion primer sequence. In one embodiment, the second primer binding sequence is an emulsion primer binding sequence.

In one embodiment, the present invention contemplates a composition comprising a ligated forked adapter pair, wherein said adapter pair comprises a first duplex DNA sequence ligated to a second duplex DNA sequence, said first duplex DNA sequence comprising a first nucleic acid sequence ligated to a first primer sequence and a second nucleic acid sequence ligated to a first primer binding sequence, and said second duplex DNA sequence ligated to a third nucleic acid sequence ligated to a second primer sequence and a fourth nucleic acid sequence ligated to a barcode. In one embodiment, the first primer sequence is an emulsion primer sequence. In one embodiment, the first primer binding sequence is an emulsion primer binding sequence. In one embodiment, the second primer sequence is an emulsion primer sequence.

In one embodiment, the present invention contemplates a method, comprising: a) providing; i) a first forked end adapter comprising a first duplex DNA sequence, wherein said first duplex DNA sequence comprises a first nucleic acid sequence ligated to a first primer sequence and a second nucleic acid sequence ligated to a second primer binding sequence; ii) a second forked end adapter comprising a second duplex DNA sequence, wherein said second duplex DNA sequence comprises a third nucleic acid sequence ligated to third primer sequence and a fourth nucleic acid sequence ligated to a fourth primer binding sequence; iii) a genomic DNA fragment capable ligating said first duplex DNA sequence to said second duplex DNA sequence; iv) a second primer capable of binding to said second primer binding sequence; v) a fourth primer capable of binding to a fourth primer binding sequence; and vi) a bead comprising said first primer and said third primer, wherein said first and third primers are attached at the 5' end; b) contacting said genomic DNA fragment with said first forked end adapter and said second forked end adapter wherein said genomic DNA fragment legates between said first duplex sequence and said second duplex sequence, thereby forming a ligated forked adapter primer pair; c) emulsion amplifying said ligated forked adapter primer pair with said bead, said second primer and said fourth primer, thereby co-localizing a first doubled stranded bead product and a second double stranded bead product on said bead. In one embodiment, the method further comprises denaturing said first double stranded bead product and said second double stranded bead product, thereby forming a first single stranded bead product and a second single stranded bead product. In one embodiment, The method further comprises hybridizing a first sequencing primer to said first single stranded bead product and a second sequencing primer to said second single stranded bead product. In one embodiment, the method further comprises sequentially sequencing said first single stranded bead product and said second single strand bead product. In one embodiment, the sequencing comprises high throughput sequencing. In one embodiment, the first sequencing primer and said second sequencing primer are high throughput sequencing primers. In one embodiment, the second forked adapter contains a barcode sequence such that the second single stranded bead product constitutes a high-quality individual read of a barcode associated with the sample such that multiple beads with different sample can be sequenced together.

In one embodiment, the present invention contemplates a kit, comprising: a) a first container comprising a first forked adapter nucleic acid sequence; b) a second container comprising a second forked adapter nucleic acid sequence; c) a third container comprising a plurality of emulsion polymerase chain reaction primers; and d) a fourth container comprising a plurality of high throughput sequencing primers and e) instructional materials containing directions providing for the use of said nucleic acids and reagents to perform paired-end sequencing of genomic nucleic acid sequence from a single bead. In one embodiment, the first forked adapter comprises a emulsion primer sequence and at least one emulsion primer binding site sequence. In one embodiment, the second forked adapter comprises an emulsion primer sequence and at least one emulsion primer binding site sequence, wherein the sequences are different from the first forked adapter.

DEFINITIONS

The term "forked end adapter", as used herein refers to any nucleic acid sequence comprising a duplex DNA portion wherein each respective strand of the duplex portion terminates in either an emulsion primer sequence or an emulsion primer sequence binding sequence. Usually, the duplex DNA portion is designed to facilitate ligation to any genomic DNA fragment.

The term "forked end adapter primer pair", as used herein refers to the ligation of a genomic DNA fragment between two forked end adapters, thereby forming a single nucleic acid sequence a central duplex DNA portion wherein each end terminates in two single stranded nucleic acid portions.

The term "barcode" as used herein, refers to any unique, non-naturally occurring, nucleic acid sequence that may be used to identify the originating genome of a nucleic acid fragment. Such barcodes may be sequences including but not limited to, TTGAGCCT, AGTTGCTT, CCAGTTAG, ACCAACTG, GTATAACA or CAGGAGCC. Although it is not necessary to understand the mechanism of an invention, it is believed that the barcode sequence provides that the second single stranded bead product constitutes a high-quality individual read of a barcode associated with a sample such that multiple beads with different samples can be sequenced together.

The term "ligation" and "ligating" as used herein, refers to any method that forms two covalent phosphodiester bonds between 3' hydroxyl ends of one nucleotide, ("acceptor") with the 5' phosphate end of another ("donor"). ATP is required for the ligase reaction, which proceeds in three steps: (1) adenylation (addition of AMP) of a residue in the active center of the enzyme, pyrophosphate is released; (2) transfer of the AMP to the 5' phosphate of the so-called donor, formation of a pyrophosphate bond; (3) formation of a phosphodiester bond between the 5' phosphate of the donor and the 3' hydroxyl of the acceptor. For example, ligation may be easily performed by contacting nucleic acids with a DNA ligase enzyme (i.e., for example, (EC 6.5.1.1).

The term "solid support", as used herein refers to any material configured to chemically bond (i.e., for example, covalently and/or non-covalently) with a nucleic acid including but not limited to plastic, latex, glass, metal (i.e., for example, a magnetized metal), nylon, nitrocellulose, quartz, silicon, or ceramic. For example, a solid support may be roughly spherical (i.e., for example, a bead).

The term "clone library", as used herein, refers to any population of organisms, each of which carries a DNA molecule inserted into a cloning vector, or alternatively, to a collection of all of the cloned vector molecules representing a specific genome.

The term "vector", as used herein refers to any plasmid or bacteriophage that has been used to infect a microorganisms, comprising at least one nucleotide sequence of interest that is preserved as an insert.

The term "library", as used herein refers to a clone library, or alternatively, a library of genome-derived sequences carrying vector sequences. The library may also have sequences allowing amplification of the "library" by the polymerase chain reaction or other in vitro amplification methods well known to those skilled in the art. The library may also have sequences that are compatible with next-generation high throughput sequencers including but not limited to Illumina adapter pair sequences.

The term "short read" as used herein refers to any nucleic acid sequence of ranging between approximately 25-500 base pairs, but preferably ranging between 50-300 base pairs, but even more preferably ranging between approximately 75-150 base pairs, but most preferably approximately 100 base pairs that is compatible with a high throughput sequencer.

The term "next-generation sequencing platform" as used herein, refers to any nucleic acid sequencing device that utilizes massively parallel technology. For example, such a platform may include, but is not limited to, Illumina sequencing platforms.

The term "high throughput sequencer adapter pair" refers to a specific nucleic acid pair that provides compatibility with a massively parallel sequencing platform (i.e., for example, Illumina sequencer adapter pairs).

The term "genome" as used herein, refers to a complete collection of genes representing a specific organism. For example, the genome may represent a microbial genome or a mammalian genome.

The term "coverage" as used herein, refers to an average number of reads representing a given nucleotide in the reconstructed sequence. It can be calculated from the length of the original genome (G), the number of reads (N), and the average read length (L) as NL/G. For example, a hypothetical genome with 2,000 base pairs reconstructed from 8 reads with an average length of 500 nucleotides will have 2× redundancy. This parameter also enables one to estimate other quantities, such as the percentage of the genome covered by reads (the coverage). A high coverage in shotgun sequencing is desired because it can overcome errors in base calling and assembly. The subject of DNA sequencing theory addresses the relationships of such quantities. Alternatively, the term "coverage" may refer to the average number of genome fragments present in a library covering a given nucleotide in the underlying genome.

The term "chain termination" as used herein, refers to any chemical reaction leading to the destruction of a reactive intermediate in a chain propagation step in the course of a polymerization, effectively bringing it to a halt. For example, chain termination may be used in the sequencing of nucleic acid polymers.

The term "bridge amplification' as used herein refers to any polymerase chain reaction that allows the generation of in situ copies of a specific DNA molecule on an oligo-decorated solid support. For example, bridge amplification is performed to produce DNA molecules that are compatible with an Illumina sequencing techniques.

The term "DNA sequencing" as used herein, refers to any methods for determining the order of the nucleotide bases—adenine, guanine, cytosine, and thymine—in a molecule of DNA.

The term "derived from" as used herein, refers to the source of a compound or sequence. In one respect, a compound or sequence may be derived from an organism or particular species. In another respect, a compound or sequence may be derived from a larger complex or sequence.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "genomic nucleic acid" as used herein refers to a naturally occurring nucleic acid sequence derived from a biological sample.

The term "an isolated nucleic acid", as used herein, refers to any nucleic acid molecule that has been removed from its natural state (e.g., removed from a cell and is, in a preferred embodiment, free of other genomic nucleic acid).

The term "portion" when used in reference to a nucleotide sequence refers to fragments of that nucleotide sequence. The fragments may range in size from 5 nucleotide residues to the entire nucleotide sequence minus one nucleic acid residue.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

An oligonucleotide sequence which is a "homolog" is defined herein as an oligonucleotide sequence which exhibits greater than or equal to 50% identity to a sequence, when sequences having a length of 100 bp or larger are compared.

Low stringency conditions comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length. is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0$ t or $R_0$ t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. As indicated by standard references, a simple estimate of the $T_m$ value may be calculated by the equation: $T_m$=81.5+0.41 (% G+C), when a nucleic acid is in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out either in vivo, i.e., for example by growing *E. coli* cells harboring recombinant (insert-containing) plasmid or fosmid vectors, or in vitro, i.e. for example using polymerase chain reaction. Dieffenbach C. W. and G. S. Dveksler (1995) In: *PCR Primer, a Laboratory Manual*, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. With PCR, it is also possible to amplify a complex mixture (library) of linear DNA molecules, provided they carry suitable universal sequences on either end such that universal PCR primers bind outside of the DNA molecules that are to be amplified.

As used herein, the term "primer" and "emulsion primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

The term "sequencing primer" as used herein, refers to a specific nucleotide sequence configured to initiate amplification for high throughput sequencer platforms, including but not limited to Illumina, SOLiD or 454.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "in operable combination" as used herein, refers to any linkage of nucleic acid sequences in such a manner that the nucleic acid molecules are capable of performed a coordinated function.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

BRIEF DESCRIPTION OF THE FIGURES

FIG. 1A: A first forked end adaptor having a first duplex DNA fragment having a first emulsion primer sequence (A) ligated to first nucleic acid sequence (D) and a second emulsion primer binding sequence (F) ligated to a second nucleic acid sequence (D').

FIG. 1B: A second forked end adaptor having second duplex DNA fragment having a third emulsion primer sequence (B) ligated to third nucleic acid (C') and a fourth emulsion primer binding sequence (E) ligated to a further nucleic acid sequence (C).

FIG. 3A: Solution phase ePCR cDNA product of the forked adapter primer pair E-C-D-A sequences shown in FIG. 1. Fourth emulsion primer (E') is shown hybridizing to the fourth emulsion primer binding sequence (E). Blue Arrow: A first strand of a genomic DNA fragment. Purple Arrow: A first recombinant strand complementary to the first genomic DNA fragment strand.

FIG. 3B: Solution phase ePCR cDNA products of the forked adapter primer pair B-C'-D'-F' sequences shown in FIG. 1. Second emulsion primer (F') is shown hybridizing to the second emulsion primer binding sequence (F). Black Arrow: A second strand of a genomic DNA fragment. Gray Arrow: A second recombinant strand complementary to the second genomic DNA fragment strand.

FIG. 3C: Bead-bound ePCR product of the forked adapter primer pair A-D-C-E sequences and F'-D'-C'-B sequences.

FIG. 6A: Dual fluorescence from all beads attached to either a first strand or a second strand of a genomic DNA fragment.

FIG. 6B: Single green fluorescence showing all beads attached to a first strand of a genomic DNA fragment.

FIG. 6C: Single red fluorescence showing all beads attached to a second strand of a genomic DNA fragment.

DETAILED DESCRIPTION OF THE INVENTION

Figure 1:
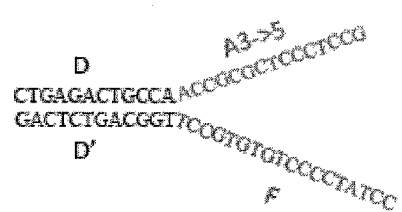
FIG. 1 presents one embodiment of a forked end adapter pair.
Figure 1:
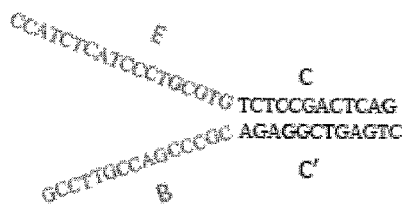

The present invention is related to genomic nucleotide sequencing. In particular, the invention describes a paired end sequencing method that enables the sequencing of unique read pairs by co-localizing both 5' ends on a single emulsion polymerase chain reaction bead. The method may use a customized forked adaptor primer pair that is compatible with massively parallel sequencing techniques. The compositions and methods disclosed herein contemplate sequencing complex genomes, amplified genomic regions, as well as detecting chromosomal structural rearrangements.

I. Conventional Emulsion-Based Polymerase Chain Reaction (ePCR)

High throughput analysis of single molecules using emulsions has been previously reported. Tawfik et al., "Man-made cell-like compartments for molecular evolution" *Nat. Biotechnol.* 16:652-656 (1998). Recently, however, emulsion technology has been applied to next-generation sequencing. Shendure et al., "Accurate multiplex polony sequencing of an evolved bacterial genome" *Science* 309: 1728-1732 (2005). Emulsion technology that is compatible with next-generation sequencing usually involves a method for capturing the contents from the emulsion droplets. For example, one approach has been described to amplify single DNA molecules onto beads for detection and enumeration of genetic variation. (i.e., for example, BEAMing, for "beads, emulsion, amplification, and magnetics.") that has been used as one approach for emulsion PCR (ePCR). Dressman et al., "Transforming single DNA molecules into fluorescent magnetic particles for detection and enumeration of genetic variations" *Proc. Natl. Acad. Sci. USA* 100:8817-8822 (2003). DNA bound to beads generated during ePCR was capable of providing a template for high-throughput sequencing. Although it is not necessary to understand the mechanism of an invention, it is believed that ePCR can amplify a single molecule of DNA into many clonal molecules per bead. Due to that belief, a number of next-generation sequencing approaches utilize emulsions and beads for DNA amplification prior to high throughput sequencing. Shendure et al., "Next-generation DNA sequencing" *Nat. Biotechnol.* 26:1135-1145 (2008); Metzker, M. L., "Sequencing technologies—the next generation" *Nat. Rev. Genet* 11:31-46 (2010); Ansorge W. J., "Next-generation DNA sequencing techniques" *N. Biotechnol.* 25:195-203; Fullwood et al., "Next-generation DNA sequencing of paired-end tags (PET) for transcriptome and genome analyses" *Genome Res.* 19:521-532 (2009); and Mardis E. R., "Next-generation DNA sequencing methods" *Annu. Rev. Genomics Hum. Genet.* 9:387-402 (2008).

An alternative approach to amplify DNA for next-generation sequencing is the bridge amplification strategy (i.e., for example, Illumina-compatible amplification). Bing et al., promega.com/geneticidproc/ussymp7proc/0726. Bridge amplification uses a single aqueous compartment; however, the individual amplicons are constrained by primers bound to a solid phase that are extended and amplified. As the name implies, the extension product from one primer forms a bridge to the other primer. Pemov et al., "DNA analysis with multiplex microarray-enhanced PCR" *Nucleic Acids Res.* 33:e11 (2005).

Conventional ePCR has been applied to next-generation DNA sequencing. Porreca et al., "Polony DNA sequencing" *Curr. Protoc. Mol. Biol. Chapter* 7:Unit 7.8 (2006). Most of the next-generation sequencing approaches are restricted to short read lengths, such that optimization of human genome resequencing can be improved with either mate-paired or paired-end sequencing technologies. However, the construction of mate-paired libraries for next-generation sequencing is difficult and time-consuming (10). What is needed in the art are improved techniques for ePCR to overcome these limitations.

A. Dual Primer Emulsion Amplification

One recent improvements in emulsion PCR has resulted in a report describing an approach called dual primer emulsion PCR (DPePCR). Xu et al., "Dual primer emulsion PCR for next-generation DNA sequencing" *BioTechniques* 48:409-412 (2010). DPePCR combines concepts from both emulsion PCR and bridge amplification for the generation of simple fragment libraries for paired-end next-generation sequencing. The DPePCR strategy can amplify short DNA fragments (less than ~300 bp, including genome fragment and primers) and enables sequencing of both ends of a DNA fragment. Although it is not necessary to understand the mechanism of an invention, it is believed that sequencing from both ends of a DNA fragment shortens library preparation time and increases the library complexity when compared with the construction of a mate-paired DNA library.

To perform DPePCR, both forward and reverse primers are attached to 1-µm beads. Additionally, since the amplicons are confined to the droplets, the amplification efficiency may be increased by including free primers in the aqueous phase. After ~120 PCR cycles, DPePCR has been reported to amplify a single DNA fragment in an emulsion drop. While the DNA is bound to the bead in a highly stable double-stranded state, one disadvantage of this method is that when under denaturing conditions, the double-stranded state immediately reforms, which inhibits the ability to sequence the DNA. To overcome this disadvantage, DPePCR must be performed with type II recognition enzyme sites (i.e., BceAI and AcuI) that are placed at the ends of the amplicons. Consequently, the DPePCR product is then be digested with restriction enzymes (i.e., BceAI and AcuI), and capping adaptors are ligated to the free end of the dsDNA before sequencing can begin. DPePCR products are sequenced using standard sequencing by ligation (SBL). The SBL sequencing strategy for DPePCR beads is identical to sequencing from standard ePCR beads. However, because of the presence of two paired-end fragments, both ends are sequenced independently, but in opposite directions. One strand is sequenced in the 3'→5' direction and the other strand is sequenced in the 5'→3' direction requiring a total of four different anchor primers.

II. Forked Adapter Primer Pair Emulsion Amplification

Figure 2:
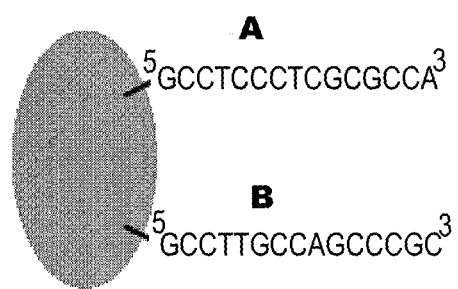
FIG. 2 presents one embodiment of a dual primed bead, wherein the first emulsion primer sequence (A) and the third emulsion primer sequence (B) are attached to the bead at their 5' end.
Figure 3:
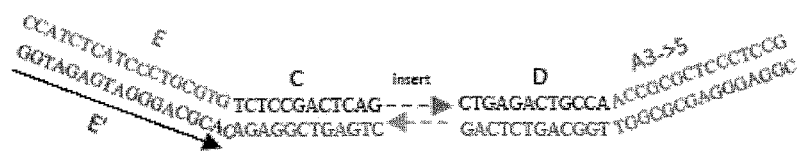
FIG. 3 presents one embodiment of an emulsion polymerase chain reaction (ePCR) amplification products of forked end adaptor primer pairs.
Figure 3:
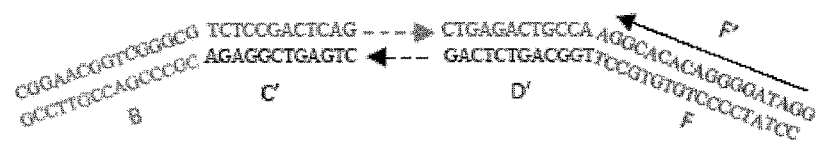
Figure 3:
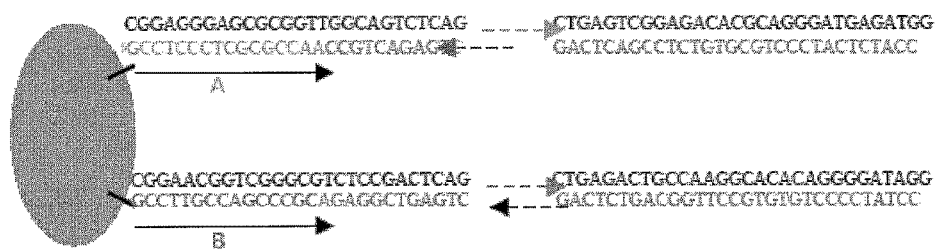
Figure 4:
FIG. 4 shows one embodiment of a bead comprising 5' attachment of the first strand (Blue Arrow) and second strand (Black Arrow) from a genomic DNA sequence configured with sequencing primers.

In some embodiments, the present invention contemplates a method using a pair of specially designed forked oligonucleotide adapters. See, FIG. 1. In one embodiment, these forked adapters 'tail' a double-stranded DNA fragment and form a forked adaptor primer pair. See, FIG. 3, colored arrow inserts. In one embodiment, each forked end of the primer pair is ligated to a different emulsion primer (i.e., for example, primer A: 5'-GCCTCCCTCGCGCCA-3'; and primer B; 5'-GCCTTGCCAGCCCGC-3') wherein each emulsion primer is also attached in a 5' orientation to a single bead for use in ePCR. See, FIG. 2. In one embodiment, each forked end of the primer pair is also ligated to two emulsion primer binding sites (i.e., for example, primer binding site E, and primer binding site F). During ePCR, emulsion primer E' (5'-GGTAGAGTAGGGACGCACC-3') and emulsion primer F' (5'-GGATAGGGGACACAC-GGA-3') are contacted with their respective forked adapter binding sites, such that each strand of the forked adapter primer pair is emulsion amplified both in solution, and on the surface of the same bead. See, FIGS. 3A/B and FIG. 3C, respectively. Once both DNA strands of the forked end adapter pair has been amplified on the bead, two distinct sequencing reactions can be performed simultaneously to read the sequence at either end of the fragment using, for example, Read 1 sequencing primer (5'-TAGGGACGCACAGAGG-CTG-3' and Read 2 sequencing primer (5'-GGACACACGGAAC-CGTCAG-3'). See, FIG. 4.

III. Conventional Cloning Libraries

Figure 7:
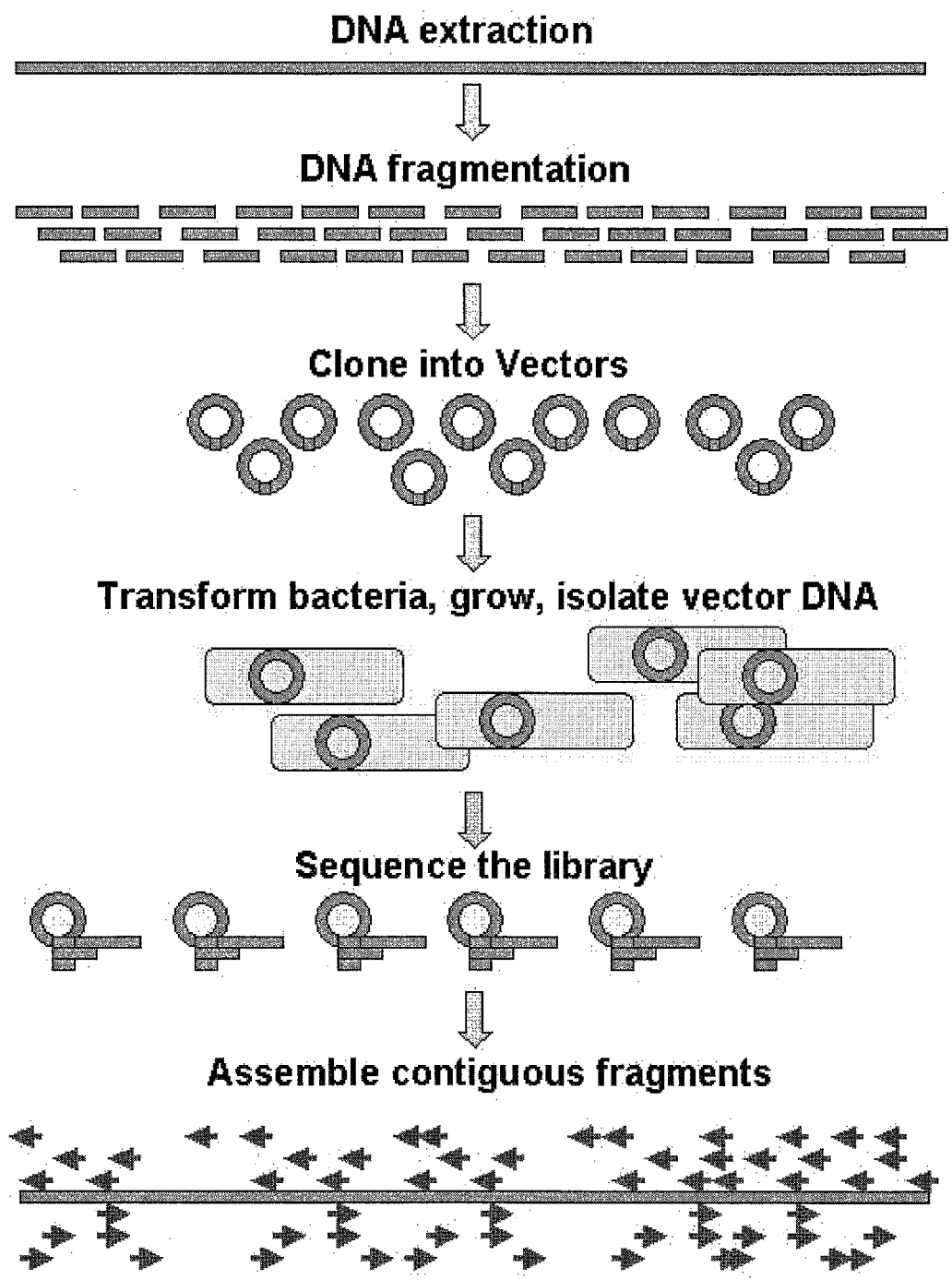
FIG. 7 presents an illustrative schema for the construction of clonal sequencing libraries. Genomic DNA is fragmented into random pieces and cloned as a bacterial library. DNA from individual bacterial clones is sequenced and the sequence is assembled by using overlapping DNA regions.

In molecular biology, a clone library is generally understood as a collection of DNA fragments that is stored and propagated in a population of microorganisms (i.e., for example, E. coli) through the process of molecular cloning. Several different types of DNA libraries have been reported, including, but not limited to, cDNA libraries that are formed from reverse-transcribed RNA and genomic libraries that formed from fragmented genomic DNA. DNA library technology has been developed for many different applications depending upon the source of the original DNA fragments. Further, there are differences in cloning vectors and techniques used in library preparation but, in general, each DNA fragment is uniquely inserted into a cloning vector, wherein a pool of recombinant DNA molecules are then transferred into a population of microorganisms. On average, each microorganism contains one nucleotide construct (i.e., for example, a vector comprising a nucleotide fragment insert). As the population of microorganisms is grown in culture, the DNA inserts are replicated as the microorganisms propagate (i.e., for example, cloned). See, FIG. 7.

A. cDNA Libraries

A cDNA library may represent a sample of the mRNA purified from a particular source (i.e., for example, a collection of cells, a particular tissue, or an entire organism), which has been converted back to a DNA template by reverse transcriptase. Thus, a cDNA library represents genes that were being actively transcribed when the mRNA was purified. Alternatively, cDNA libraries can be generated using techniques that promote "full-length" clones or under conditions that generate shorter fragments used for the identification of "expressed sequence tags".

cDNA libraries are useful in reverse genetics, but they only represent a very small (less than 1%) portion of the overall genome in a given organism. Applications of cDNA libraries include, but are not limited to, discovery of novel genes, cloning of full-length cDNA molecules for in vitro study of gene function, mRNA expression profiling, or mRNA alternative splicing patterns.

B. Genomic Libraries

A genomic library may be a set of clones that together represent an entire genome of a given organism (i.e., for example, DNA). The number of individual microbial clones that constitute a genomic library depends on: i) the size of the genome in question; and ii) the DNA insert size tolerated by the particular cloning vector system. For most practical purposes, the tissue source of the genomic DNA is unimportant because each cell of the body contains virtually identical DNA. Useful applications of genomic libraries include, but are not limited to, determining the complete genome sequence of a given organism, serving as a source of genomic sequence for generation of transgenic animals through genetic engineering, identifying regulatory sequence function, and/or identifying genetic mutations responsible for medical conditions.

C. Microbial Transformation

1. Plasmids

A plasmid has been explained to be a DNA molecule that is separate from, and can replicate independently of, the chromosomal DNA. In: Plasmids: Current Research and Future Trends. Lipps G (editor). Caister Academic Press. ISBN 978-1-904455-35-6 (2008). Plasmid DNA may be double stranded and in many cases, spontaneously circularizes. Plasmids usually occur naturally in bacteria, but are sometimes found in eukaryotic organisms (e.g., a 2-micrometer-ring in *Saccharomyces cerevisiae*).

Plasmid size varies from 1 to over 1,000 kilobase pairs (kbp). In: Molecular cloning: a laboratory manual. Russell et al. Cold Spring Harbor, N.Y: Cold Spring Harbor Laboratory (2001): Barnett et al., "Nucleotide sequence and predicted functions of the entire *Sinorhizobium* meliloti pSymA megaplasmid" *PNAS* 98:9883 (2001); Finan et al., "The complete sequence of the 1,683-kb pSymB megaplasmid from the N2-fixing endosymbiont" *PNAS* 98:9889 (2001). The number of identical plasmids within a single cell can range anywhere from one to several thousands.

Plasmids are considered transferable genetic elements, or "replicons", capable of autonomous replication within a suitable host. Similar to viruses, plasmids are not considered a form of "life" as it is currently defined. Simkovics et al., "The Origin and evolution of viruses (a review)" *Acta Microbial Immunol Hung* 45:349-390 (1998). Unlike viruses, plasmids are considered "naked" DNA and do not encode genes necessary to encase the genetic material for transfer to a new host. Plasmid host-to-host transfer requires direct, mechanical transfer by "conjugation" or changes in host gene expression allowing active uptake of the plasmid by "transformation". Microbial transformation with plasmid DNA also provides a mechanism for horizontal gene transfer within a population of microorganisms.

2. Vectors

Plasmids used in genetic engineering are generally referred to as vectors. Vectors serve as important tools in genetics and biotechnology labs, where they are commonly used to facilitate the expression of integrated genes. Many vectors are commercially available for such uses. For example, a gene desired for replication may be inserted into copies of a vector containing genes that make cells resistant to particular antibiotics, for inserting a multiple cloning site (MCS), and/or a polylinker site. An MCS comprises a short region containing several commonly used restriction sites allowing the easy insertion of DNA fragments at this location. Next, the vectors are inserted into a microorganism (i.e., for example, a bacteria including, but not limited to, *E. coli*) by transformation. Then, the bacteria are exposed to the antibiotic for which the vector imparts a genetic resistance. Consequently, only microorganisms which stably incorporate the vector survive. The microorganisms comprising the vector can be generated into libraries.

However, conventional cloning vectors can usually only contain nucleotide inserts of about 1-10 kb. To clone longer lengths of DNA, lambda phage with lysogeny genes deleted, cosmids, fosmids, bacterial artificial chromosomes or yeast artificial chromosomes could be used.

3. DNA Extraction

In some techniques, the integrated sequences within a vector and/or plasmid are often purified away from the rest of the genome and allows these integrated sequences to be uses to construct other vectors and/or molecular cloning library generation. There are several methods to isolate and purify such plasmid DNA from bacteria, including, but not limited to, the miniprep, the maxiprep, or the bulkprep. The yield is a small amount of impure plasmid DNA. Maxipreps use much larger volumes of bacterial suspension. Essentially, maxipreps are a scaled-up miniprep followed by additional purification. This results in relatively large amounts (i.e., for example, several micrograms) of very pure plasmid DNA. These plasmid preparation methods can be used to obtain large amounts of a plasmid harboring a single cloned insert, or to obtain large amounts of a complex mixture of plasmids collectively harboring an entire library of cloned insert. Commercial kits are currently available that provide reagents and instructions to perform vector and/or plasmid extraction at various scales, purity and levels of automation.

IV. Nucleic Acid Sequencing

The term DNA sequencing refers to sequencing methods for determining the order of the nucleotide bases—adenine, guanine, cytosine, and thymine—in a molecule of DNA.

Known DNA sequences are presently used for basic biological research, diagnostics, biotechnology, forensic biology, and/or biological systematics. Recent advances in the speed of sequencing (i.e., for example, high throughput sequencing) attained with modern DNA sequencing technology has been instrumental in the sequencing of the human genome, in the Human Genome Project.

The first DNA sequences were obtained using laborious methods based on two-dimensional chromatography. Following the development of dye-based sequencing methods with automated analysis, DNA sequencing has become easier and faster. Olsvik et al., "Use of automated sequencing of polymerase chain reaction-generated amplicons to identify three types of cholera toxin subunit B in *Vibrio cholerae* O1 strains" *J. Clin. Microbiol.* 31:22-25 (1993).

A. Chain Termination Sequencing

The chain-termination method (i.e., for example, the Sanger method) introduced improvements into nucleotide sequencing technology by increasing efficiency, reducing the use of toxic chemicals and/or radioactivity than initial techniques. Chain termination sequencing introduced the use of dideoxynucleotide triphosphates (ddNTPs) as DNA chain terminators.

A classical chain-termination method usually comprises a single-stranded DNA template, a DNA primer, a DNA polymerase, radioactively or fluorescently labeled nucleotides, and modified nucleotides that terminate DNA strand elongation. The DNA sample is divided into four separate sequencing reactions, containing all four of the standard deoxynucleotides (e.g., dATP, dGTP, dCTP and dTTP) and the DNA polymerase. To each reaction is added only one of the four dideoxynucleotides (e.g., ddATP, ddGTP, ddCTP, or ddTTP) which are the chain-terminating nucleotides. These dideoxynucleotides lack a 3'-OH group required for the formation of a phosphodiester bond between two nucleotides, thus terminating DNA strand extension and resulting in DNA fragments of varying length.

Figure 8:
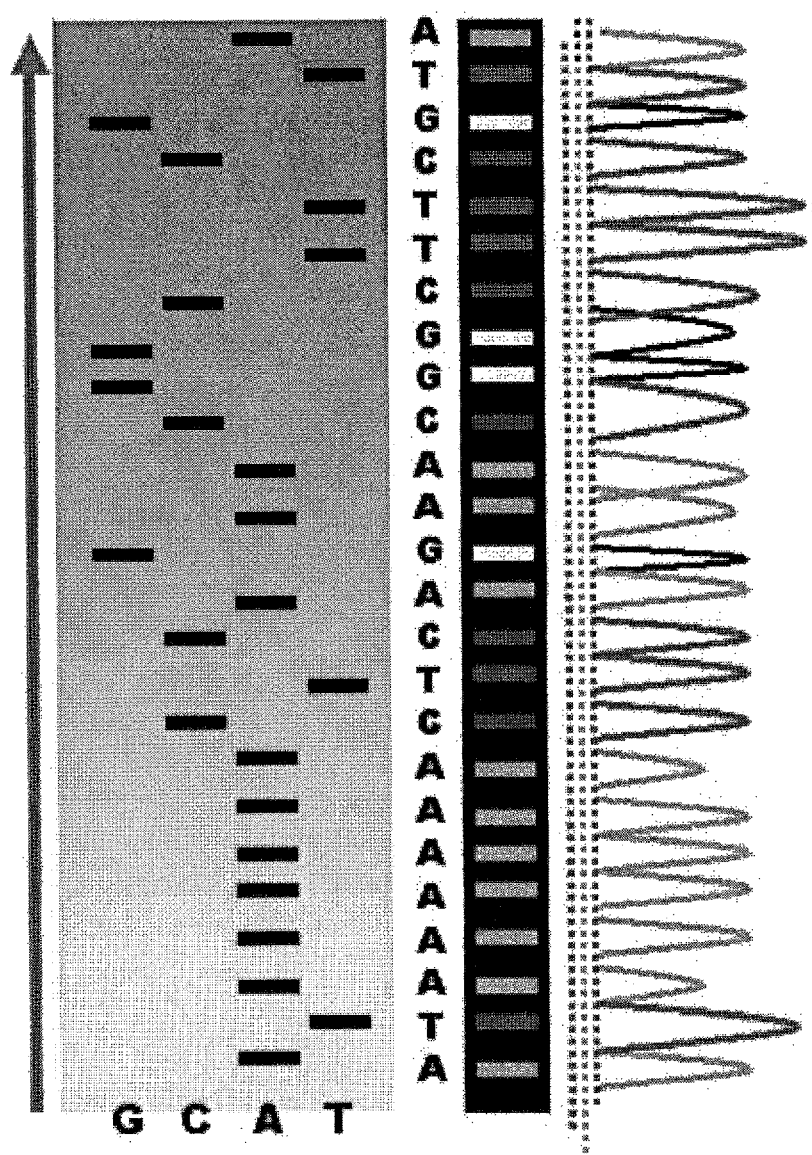
FIG. 8 presents an exemplary illustration of a Sanger chain termination nucleic acid sequence ladder (gel electrophoresis) as compared to their representative fluorescent peaks.

Newly synthesized and labeled DNA fragments are heat denatured, and separated by size (i.e., for example, with a resolution of just one nucleotide) by gel electrophoresis on a denaturing polyacrylamide-urea gel with each of the four reactions run in one of four individual lanes (lanes A, T, G, C); the DNA bands are then visualized by autoradiography or UV light, and the DNA sequence can be directly read off the X-ray film or gel image, wherein dark bands on the gel correspond to DNA fragments of different lengths. For example, a dark band in a lane indicates a DNA fragment that is the result of chain termination after incorporation of a dideoxynucleotide (ddATP, ddGTP, ddCTP, or ddTTP). The relative positions of the different bands among the four lanes are then used to read (from bottom to top) the DNA sequence. See, FIG. 8.

B. Next-Generation Sequencing

Next-generation sequencing technologies (i.e., for example, high throughput sequencing) parallelize the sequencing process and results in a low-cost method that simultaneously produces thousands or millions of sequences. Hall N., "Advanced sequencing technologies and their wider impact in microbiology" *J. Exp. Biol.* 210 (Pt 9): 1518-1525 (2007); and Church G., "Genomes for all" *Sci. Am.* 294: 46-54 (2006). Advantages of next-generation sequence reads including but not limited to: i) the length of a sequence read from most current next-generation platforms is shorter than that from a capillary sequencer; and ii) each next-generation read type has a unique error model different from that already established for capillary sequence reads. Both differences affect how the reads are utilized in bioinformatic analyses, depending upon the application. For example, in strain-to-reference comparisons (i.e., for example, re-sequencing), the typical definition of repeat content must be revised in the context of the shorter read length. In addition, a much higher read coverage or sampling depth is required for comprehensive resequencing with short reads to adequately cover the reference sequence at the depth and low gap size needed. Some applications are more suitable for certain platforms than others, as detailed below. Furthermore, read length and error profile issues entail platform- and application-specific bioinformatics-based considerations. Moreover, it is important to recognize the significant impacts that implementation of these platforms in a production sequencing environment has on informatics and bioinformatics infrastructures.

Several techniques for massively parallel DNA sequencing have recently been described. Ronaghi et al., "Analyses of secondary structures in DNA by pyrosequencing" *Anal Biochem* 267: 65-71 (1999); Brenner et al., "Gene expression analysis by massively parallel signature sequencing (MPSS) on microbead arrays" *Nat Biotechnol* 18:630-634 (2000); Braslaysky et al., Sequence information can be obtained from single DNA molecules" *Proc Natl Acad Sci* 100:3960-3964 (2003); Margulies et al., "Genome sequencing in microfabricated high-density picoliter reactors" *Nature* 437:376-380 (2005); Shendure et al., "Accurate multiplex polony sequencing of an evolved bacterial genome" *Science* 309:1728-1732 (2005); Ju et al., "Four-color DNA sequencing by synthesis using cleavable fluorescent nucleotide reversible terminators" *Proc Natl Acad Sci* 103:19635-19640 (2006); Gibbs et al., "Evolutionary and biomedical insights from the rhesus macaque genome" *Science* 316:222-234 (2007); Bentley et al., "Accurate whole human genome sequencing using reversible terminator chemistry" *Nature* 456:53-59 (2008); and Eid et al., "Real-time DNA sequencing from single polymerase molecules" *Science* 323:133-138 (2009).

These techniques broadly fall into at least two assay categories (i.e., for example, polymerase and/or ligase based) and/or at least two detection categories (i.e., for example, asynchronous single molecule and/or synchronous multi-molecule readouts). For example, SOLiD (Sequencing by Oligo Ligation Detection) sequencing comprises a DNA ligase-based synchronous ensemble detection method utilized to read 500 million to over 1 billion reads per instrument run. Cloonan et al., "Stem cell transcriptome profiling via massive-scale mRNA sequencing" *Nat Methods* 5:613-619 (2008); and Valouev et al., "A high-resolution, nucleosome position map of *C. elegans* reveals a lack of universal sequence-dictated positioning" *Genome Res* 18:1051-1063 (2008).

All of these techniques are theoretically compatible with mate-paired sequencing, but they differ in how they generate the mate-paired reads. For example, one approach generates short pairs from cluster polymerase chain reaction (PCR) colonies often referred to as "paired-ends." Campbell et al., "Identification of somatically acquired rearrangements in cancer using genome-wide massively parallel paired-end sequencing" *Nat Genet* 40: 722-729 (2008). These paired-end reads have limited insert sizes due to the efficiency and representation of PCR amplification of long amplicons via cluster PCR. Consequently, very few paired-end reads are generated that are longer than a Sanger capillary electrophoresis read ($<10^3$ clone coverage in pairs >1.0 kb).

DNA circularization and random shearing have been used, thereby circumventing the need to PCR amplify the entire pairing distance at the cost of more input DNA. Korbel et al., "Paired-end mapping reveals extensive structural variation in the human genome" *Science* 318: 420-426 (2007); and Bentley et al., "Accurate whole human genome sequencing using reversible terminator chemistry" *Nature* 456:53-59 (2008). These pairs each differ substantially in their tag length due to the random shearing step. The asymmetrical tag lengths reduce the pairing efficiency and often contaminate the library prep with a high number of 200-bp inserts; thus, no more than 100× clone coverage is obtained, and many tags are sequenced that are not paired or are paired in the wrong distance or orientation. Furthermore, these techniques may result in many inverted molecules that complicate the detection of inversions.

A preferred pairing method would provide both high sequence coverage and high clone or "physical" coverage with flexible insert sizes such that SNPs, small indels, larger structural variations, and copy number variants (CNVs) could be surveyed in one method. Two pairing methods can be used that retain less variable tag lengths while enabling both high sequence coverage and high clone coverage of the human genome to enable the broadest survey of variation possible. Use of ligases for massively parallel short-read DNA sequencing of human genomes offers several unique attributes next to polymerases. Most notable is the use of an error-correcting probe-labeling scheme (two-base encoding, or 2BE), which provides error correction concurrent with the color-called alignment of the data (i.e., for example, without having to resequence the reads). This correction property has specific utility in bisulfite sequencing, de novo assembly, indel detection, and SNP detection.

SOLiD sequencing is believed capable of efficiently surveying single nucleotide polymorphisms and many forms of structural variation concurrently at relatively modest coverage levels. Such an expansive clone coverage allows identification of a larger number of structural variants in a size range not efficiently explored in previous studies.

The massively parallel scale of sequencing implies a similarly massive scale of computational analyses that include image analysis, signal processing, background subtraction, base calling, and quality assessment to produce the final sequence reads for each run. In every case, these analyses place significant demands on the information technology (IT), computational, data storage, and laboratory information management system (LIMS) infrastructures extant in a sequencing center, thereby adding to the overhead required for high-throughput data production. This aspect of next-generation sequencing is at present complicated by the dearth of current sequence analysis tools suited to shorter sequence read data; existing data analysis pipelines and algorithms must be modified to accommodate these shorter reads. In many cases, and certainly for new applications of next-generation sequencing, entirely new algorithms and data visualization interfaces are being devised and tested to meet this new demand. Therefore, the next-generation platforms are effecting a complete paradigm shift, not only in the organization of large-scale data production, but also in the downstream bioinformatics, IT, and LIMS support required for high data utility and correct interpretation.

This paradigm shift promises to radically alter the path of biological inquiry, as the following review of recent endeavors to implement next-generation sequencing platforms and accompanying bioinformatics-based analyses serves to substantiate.

Most massively parallel high throughput sequencing techniques avoid molecular cloning in a microbial host (i.e., for example, transformed bacteria, such as *E. coli*) to propagate the DNA inserts. Instead, they use in vitro clonal PCR amplification strategies to meet the molecular detection sensitivities of the current molecule sequencing technologies. Some sequencing platforms (e.g., Helicos Biosciences) avoid amplification altogether and sequence single, unamplified DNA molecules. With or without clonal amplification, the available yield of unique sequencing templates has a significant impact on the total efficiency of the sequencing process. Various clonal amplification methods have been described in more detail below 1. Emulsion Amplification Emulsion PCR is generally used to isolate individual DNA molecules along with primer-coated beads in aqueous droplets within an oil phase. An ensuing polymerase chain reaction process then coats each bead with clonal copies of the DNA molecule followed by immobilization for later sequencing. Emulsion PCR is more commonly referred to as: i) 454 sequencing (Margulies et al., "Genome sequencing in microfabricated high-density picoliter reactors" *Nature* 437:376-380 (2005); ii) polony sequencing (Shendure, J. "Accurate Multiplex Polony Sequencing of an Evolved Bacterial Genome" *Science* 309:1728 (2005); and iii) SOLiD sequencing (Applied Biosystems).

454 sequencing techniques employ pyrosequencing that uses DNA polymerization by adding one nucleotide species at a time and detecting and quantifying the number of nucleotides added to a given location through the light emitted by the release of attached pyrophosphates. Ronaghi et al., "Real-time DNA sequencing using detection of pyrophosphate release" *Analytical Biochemistry* 242: 84-89 (1996).

The SOLiD platform uses an adapter-ligated fragment library similar to those of the other next-generation platforms, and uses an emulsion PCR approach with small magnetic beads to amplify the fragments for sequencing. Unlike the other platforms, SOLiD uses DNA ligase and a unique approach to sequence the amplified fragments. Two flow cells are processed per instrument run, each of which can be divided to contain different libraries in up to four quadrants. Read lengths for SOLiD are user defined between 25-50 bp, and each sequencing run yields up to ~100 Gb of DNA sequence data. Once the reads are base called, have quality values, and low-quality sequences have been removed, the reads are aligned to a reference genome to enable a second tier of quality evaluation called two-base encoding. The principle of two-base encoding illustrates how this approach works to differentiate true single base variants from base-calling errors.

2. Bridge Amplification

Bridge PCR also involves in vitro clonal amplification, wherein the cloned fragments are amplified using primers that are attached to a solid surface. Such configurations are compatible with an Illumina Genome Analyzer. For example, DNA molecules are physically bound to a surface such that they may be sequenced in parallel (i.e., for example, known in the art as massively parallel sequencing).

Sequencing by synthesis techniques (i.e., for example, dye-termination electrophoretic sequencing) uses a DNA polymerase to determine the base sequence. Alternatively, a reversible terminator method may be used wherein fluorescently labeled nucleotides are individually added, such that each position is determined in real time (i.e., for example, Illumina). A blocking group on each labeled nucleotide is then removed to allow polymerization of another nucleotide.

Massively parallel sequencing of millions of fragments has been successfully commercialized by a reversible terminator-based sequencing chemistry (Illumina). This sequencing technology offers a highly robust, accurate, and scalable system that is cost-effective, and sufficiently accurate to support next-generation sequencing technologies. For example, the Illumina sequencing technology relies on the attachment of randomly fragmented genomic DNA to a planar, optically transparent surface. These attached DNA fragments are extended and bridge amplified to create an ultra-high density sequencing flow cell with hundreds of millions of clusters, each containing ~1,000 copies of the same template. These templates are sequenced using a robust four-color DNA sequencing-by-synthesis technology that employs reversible terminators with removable fluorescent dyes. This approach ensures high accuracy and true base-by-base sequencing, eliminating sequence-context specific errors and enabling sequencing through homopolymers and repetitive sequences.

High-sensitivity fluorescence detection may be achieved using laser excitation and total internal reflection optics. Sequence reads are aligned against a reference genome and genetic differences are called using specially developed data analysis pipeline software. Alternative sample preparation methods allow the same system to be used for a range of applications including gene expression, small RNA discovery, and protein-nucleic acid interactions.

After completion of the first read, the templates can be regenerated in situ to enable a second 75+ bp read from the opposite end of the fragments. A paired-end module directs the regeneration and amplification operations to prepare the templates for the second round of sequencing. First, the newly sequenced strands are stripped off and the complementary strands are bridge amplified to form clusters. Once the original templates are cleaved and removed, the reverse strands undergo sequencing-by-synthesis. The second round of sequencing occurs at the opposite end of the templates, generating 75+ bp reads for a total of >20 Gb of paired-end data per run.

A single molecule amplification step compatible with the Illumina Genome Analyzer may start with an Illumina-specific adapter library and takes place on an oligo-derivatized surface of a flow cell. A flow cell comprises an 8-channel sealed glass microfabricated device that allows bridge amplification of fragments on its surface, and uses DNA polymerase to produce multiple DNA copies (i.e., for example, DNA clusters) wherein each cluster represents a single molecule that initiated the cluster amplification. A separate library can be added to each of the eight channels, or the same library can be used in all eight, or combinations thereof. Each cluster may contain approximately one million amplicons (e.g., copies) of the original fragment, which is sufficient for reporting incorporated bases at the required signal intensity for detection during sequencing.

The Illumina system utilizes a sequencing-by-synthesis approach in which all four nucleotides are added simultaneously to the flow cell channels, along with DNA polymerase, for incorporation into the oligo-primed cluster fragments. Specifically, the nucleotides carry a base-unique fluorescent label and the 3'-OH group is chemically blocked such that each incorporation is a unique event. An imaging step follows each base incorporation step, during which each flow cell lane is imaged in three 100-tile segments by the instrument optics at a cluster density per tile of 300,000 or more. After each imaging step, the 3' blocking group is chemically removed to prepare each strand for the next incorporation by DNA polymerase. This series of steps continues for a specific number of cycles, as determined by user-defined instrument settings, which permits discrete read lengths of 75+ bases. A base-calling algorithm assigns sequences and associated quality values to each read and a quality checking pipeline evaluates the Illumina data from each run, removing poor-quality sequences.

For example, a high-density single-molecule arrays of genomic DNA fragments may be attached to the surface of the flow cell reaction chamber and used isothermal 'bridging' amplification to form DNA 'clusters' from each fragment. In such an array, the DNA in each cluster single stranded and added a universal primer for sequencing. For paired read sequencing, the DNA templates are converted to double-stranded DNA and removed the original strands, leaving the complementary strand as template for the second sequencing reaction. To obtain paired reads separated by larger distances, DNA fragments may be circularized of the required length short junction fragments are constructed to support paired end sequencing. Bentley et al., "Accurate whole human genome sequencing using reversible terminator chemistry" *Nature* 456:53-59 (2008).

C. Shotgun Sequencing

In genetics, shotgun sequencing, also known as shotgun cloning, is generally referred to as a method used for sequencing long DNA strands. It is named by analogy with the rapidly-expanding, quasi-random firing pattern of a shotgun. Since the chain termination method of DNA sequencing can only be used for fairly short strands (i.e., for example, 100 to 1000 basepairs), longer sequences must be subdivided into smaller fragments, and subsequently re-assembled to give the overall sequence. Two principal methods are used for this: chromosome walking, which progresses through the entire strand, piece by piece, and shotgun sequencing, which is a faster but more complex process, and uses random fragments.

In shotgun sequencing, DNA is broken up randomly into numerous small segments, which have been conventionally sequenced using the chain termination method to obtain reads. Multiple overlapping reads for the target DNA are obtained by performing several rounds of this fragmentation and sequencing. Computer programs then use the overlapping ends of different reads to assemble them into a continuous sequence. Staden R., "A strategy of DNA sequencing employing computer programs" *Nucleic Acids Research* 6: 2601-2610 (1979) and Anderson S., "Shotgun DNA sequencing using cloned DNase I-generated fragments" *Nucleic Acids Research* 9:3015-3027 (1981). For example, a single nucleic acid sequence may be sequenced as two separate fragments, wherein each fragment comprises two reads, the respective 3'-5' strand and the 5'-3' strand. None of the four different reads cover the full length of the original sequence. However, the four reads can be assembled into the original sequence using nucleic acid sequence overlap of their ends, that both to align and order the respective reads. The original shotgun sequencing method had disadvantages by necessitating the processing an enormous amount of information that generated ambiguities and sequencing errors. Assembly of complex genomes is additionally complicated by the great abundance of repetitive sequence, meaning similar short reads could come from completely different parts of the sequence.

Consequently, numerous overlapping read segments for each fragment of original DNA are necessary to overcome these difficulties and accurately assemble the sequence. For example, to complete the Human Genome Project, most of the human genome was sequenced at 12× or greater coverage; that is, each base in the final sequence was present, on average, in 12 reads.

Whole genome shotgun sequencing for small (i.e., for example, 4,000 to 7,000 base pairs) genomes gave way to a broader application that benefited from pair-wise end sequencing. Pair wise end sequencing performs sequencing from both ends of a read simultaneously, instead of a linear left-right process. Although sequencing both ends of the same fragment and keeping track of the paired data was more cumbersome than sequencing a single end of two distinct fragments, the knowledge that the two sequences were oriented in opposite directions and were about the length of a fragment apart from each other was valuable in reconstructing the sequence of the original target fragment.

Paired end sequencing was first reported as part of the sequencing of the human HGPRT locus, although the use of paired ends was limited to closing gaps after the application of a traditional shotgun sequencing approach. Edwards et al., "Closure strategies for random DNA sequencing". *Methods: A Companion to Methods in Enzymology* 3: 41-47 (1991). A theoretical description of a pure pair-wise end sequencing strategy assuming fragments of constant length was also reported. Edwards et al., "Automated DNA sequencing of the human HPRT locus" *Genomics* 6:593-608 (1990). The method was improved by demonstrating that pair wise sequencing could be performed using fragments of varying sizes, thereby demonstrating a pair-wise end-sequencing strategy would be possible on large genomic targets. Roach et al., "Pair-wise end sequencing: a unified approach to genomic mapping and sequencing" *Genomics* 26:345-353 (1995). This strategy was successfully employed to sequence the genomes of *Haemophilus influenzae, Drosophila melanogaster*, and *Homo sapiens*. Fleischmann et al., "Whole-genome random sequencing and assembly of *Haemophilus influenzae* Rd.". *Science* 269 (5223):496-512 (1995); and Adams et al., "The genome sequence of *Drosophila melanogaster*". *Science* 287 (5461): 2185-2195 (2000).

To apply pair wise sequencing to high-molecular-weight DNA, the DNA can be sheared into random fragments, size-selected (i.e., for example, 2, 10, 50, and/or 150 kb), and cloned into an appropriate vector. The clones are then sequenced from both ends using the chain termination method yielding two short sequences. Each sequence is called an end-read, or read, wherein two reads from the same clone are referred to as mate pairs. Since the chain termination method usually can only produce reads between 500 and 1000 bases long, in all but the smallest clones, mate pairs will rarely overlap. The original DNA sequence is reconstructed from the numerous reads using sequence assembly software. First, overlapping reads are collected into longer composite sequences known as contigs. Contigs can be linked together into scaffolds by following connections between mate pairs. The distance between contigs can be inferred from the mate pair positions if the average fragment length of the library is known and has a narrow window of deviation. Conventional pair wise sequencing has disadvantages including but not limited to a need to improve reliability to correctly link regions, particularly for genomes with repeating regions.

Although shotgun sequencing was the most advanced technique for sequencing genomes from about 1995-2005, other technologies surfaced, called next-generation sequencing (supra). These technologies produce shorter reads (anywhere from 25-500 bps) but many hundreds of thousands or millions of reads are processed in a relatively short time (i.e., for example, within twenty-four hours). This results in high coverage, but the assembly process is much more computationally expensive. These technologies are vastly superior to chain termination shotgun sequencing due to the high volume of data and the relatively short time it takes to sequence a whole genome.

VI. Polymerase Chain Reaction

A. Conventional Polymerase Chain Reaction

The polymerase chain reaction (PCR) is a technique in molecular biology to amplify a single or few copies of a piece of DNA across several orders of magnitude, generating thousands to millions of copies of a particular DNA sequence. The method relies on thermal cycling, consisting of cycles of repeated heating and cooling of the reaction for DNA melting and enzymatic replication of the DNA. Primers (short DNA fragments) containing sequences complementary to the target region along with a DNA polymerase (after which the method is named) are key components to enable selective and repeated amplification. As PCR progresses, the DNA generated is itself used as a template for replication, setting in motion a chain reaction in which the DNA template is exponentially amplified. PCR can be extensively modified to perform a wide array of genetic manipulations.

Almost all PCR applications employ a heat-stable DNA polymerase, such as Taq polymerase, an enzyme originally isolated from the bacterium *Thermus aquaticus*. This DNA polymerase enzymatically assembles a new DNA strand from DNA building blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample to a defined series of temperature steps. These thermal cycling steps are necessary first to physically separate the two strands in a DNA double helix at a high temperature in a process called DNA melting. At a lower temperature, each strand is then used as the template in DNA synthesis by the DNA polymerase to selectively amplify the target DNA. The selectivity of PCR results from the use of primers that are complementary to the DNA region targeted for amplification under specific thermal cycling conditions. In one embodiment, the present invention contemplates a method comprising, amplifying a plurality of a complex mixture ("library") of DNA molecules by PCR, wherein each DNA molecule carries the same pair of universal terminal sequence attachments.

PCR is used to amplify a specific region of a DNA strand (the DNA target). Most PCR methods typically amplify DNA fragments of up to ~10 kilo base pairs (kb), although some techniques allow for amplification of fragments up to 40 kb in size. Cheng et al., "Effective amplification of long targets from cloned inserts and human genomic DNA" *Proc Natl Acad Sci.* 91: 5695-5699 (1994). A basic PCR set up usually involves several components and reagents. "Chapter 8: In vitro Amplification of DNA by the Polymerase Chain Reaction" In: Molecular Cloning: A Laboratory Manual (3rd ed.) Sambrook et al. (Eds). Cold Spring Harbor, N.Y.: Cold Spring Harbor Laboratory Press. ISBN 0-87969-576-5 (2001). These components may include, but are not limited to: i) DNA template that contains the DNA region (target) to be amplified; ii) two primers that are complementary to the 3' ends of each of the sense and anti-sense strand of the DNA target; iii) Taq polymerase or another DNA polymerase with a temperature optimum at around 70° C.; iv) deoxynucleoside triphosphates (dNTPs; also very commonly and erroneously called deoxynucleotide triphosphates), the building blocks from which the DNA polymerases synthesizes a new DNA strand; v) buffer solution, providing a suitable chemical environment for optimum activity and stability of the DNA polymerase; vi) divalent cations, magnesium or manganese ions; generally $Mg^{2+}$ is used, but $Mn^{2+}$ can be utilized for PCR-mediated DNA mutagenesis, as higher $Mn^{2+}$ concentration increases the error rate during DNA synthesis (Pavlov et al., "Recent developments in the optimization of thermostable DNA polymerases for efficient applications" *Trends Biotechnol.* 22: 253-260 (2004)); and vii) monovalent cation potassium ions.

The PCR is commonly carried out in a reaction volume of 10-200 μl in small reaction tubes (0.2-0.5 ml volumes) in a thermal cycler. The thermal cycler heats and cools the reaction tubes to achieve the temperatures required at each step of the reaction. Many modern thermal cyclers make use of the Peltier effect which permits both heating and cooling of the block holding the PCR tubes simply by reversing the electric current. Thin-walled reaction tubes permit favorable thermal conductivity to allow for rapid thermal equilibration. Most thermal cyclers have heated lids to prevent condensation at the top of the reaction tube, but a layer of oil or a ball of wax may also be effective.

VIII. Barcodes

DNA barcoding is a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" *Proc. Natl. Acad. Sci. U.S.A.* 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" *African Invertebrates* 51(2): 413-421 (2010); and Seberg et al., "How many loci does it take to DNA barcode a crocus?" *PLoS One* 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" *Frontiers in Zoology* 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" *PNAS* 106(31):12794-12797 (2009). Further, these putative barcode loci are believed short enough to be easily sequenced with current technology. Kress et al., "DNA barcodes: Genes, genomics, and bioinformatics" *PNAS* 105(8):2761-2762 (2008). Consequently, these loci would provide a large variation between species in combination with a relatively small amount of variation within a species. Lahaye et al., "DNA barcoding the floras of biodiversity hotspots" *Proc Natl Acad Sci USA* 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit I (COI) gene was proposed as a potential 'barcode'. As of 2009, databases of CO1 sequences included at least 620,000 specimens from over 58,000 species of animals, larger than databases available for any other gene. Ausubel, J., "A botanical macroscope" *Proceedings of the National Academy of Sciences* 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

IX. Kits

In another embodiment, the present invention contemplates kits for the practice of the methods of this invention. The kits preferably include one or more containers containing a nucleic acid sequence comprising a first forked adapter. The kit can optionally include one or more containers containing a nucleic acid sequence comprising a second forked adapter. In one embodiment, the first forked adapter comprises a emulsion primer sequence and at least one emulsion primer binding site sequence. In one embodiment, the second forked adapter comprises an emulsion primer sequence and at least one emulsion primer binding site sequence, wherein the sequences are different from the first forked adapter. The kit can optionally include a plurality of emulsion polymerase chain reaction primers. The kit can optionally include enzymes and reagents for emulsion PCR. The kit can optionally include high throughput sequencing primers compatible with either the first forked adapter sequence or the second forked adapter sequence. For example, the kit can optionally include enzymes such as DNA polymerase, Taq polymerase, PCR primers and/or restriction enzymes. The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the compositions and/or reagents in the present invention.

In one embodiment, the kit further comprises instructions for ligating a genomic nucleic acid sequence between the first and second forked adaptors to create a forked adapter primer pair. In one embodiment, the kit further comprises instructions for performing emulsion PCR on the forked adaptor primer pair, resulting in the formation of beads comprising co-localized read pairs. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXPERIMENTAL

Example I

Bead Co-Localization of Genomic Fragment DNA Strands

Streptavidin-coated magnetic beads (M280 Dynal beads, Invitrogen) were coated with a biotinylated oligo A and a biotinylated oligo B.

A DNA library was created with forked adapter primer pairs comprising oligo A and oligo B by in an emulsion PCR amplification onto beads. The amplification solution contained emulsion primers compatible with the forked adapter primer pairs and beads attached to the 5' ends of a first primer specific for oligo A and the 5' end of a second primer specific for oligo B.

Figure 5:
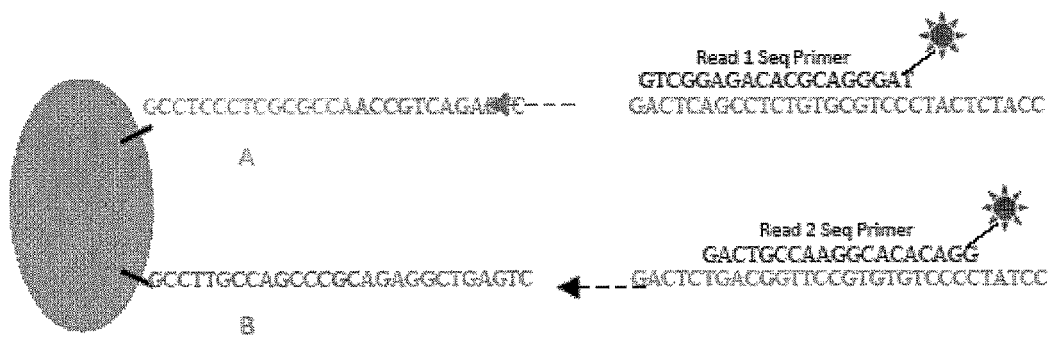
FIG. 5 presents one embodiment of an experiment to demonstrate bead co-localization of a first strand (Blue Arrow) and second strand (Black Arrow) from a genomic DNA sequence by hybridizing differentially labeled sequencing primers (i.e., for example, green fluorescent probe versus red fluorescent probe).
Figure 6:
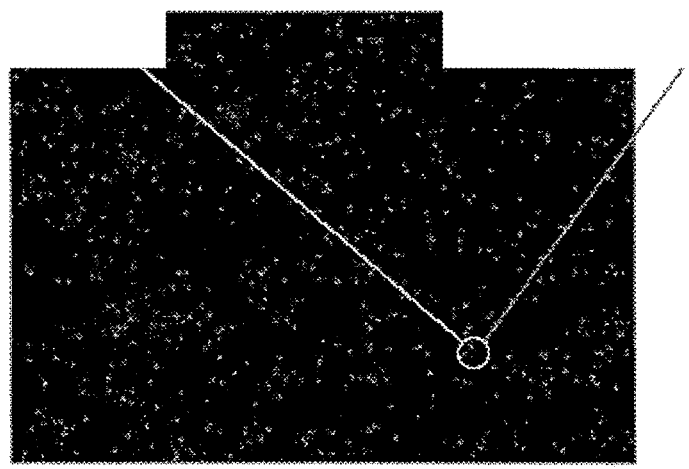
FIG. 6 presents exemplary data showing the co-localization of beads attached to the first strand and second strand of a genomic DNA fragment. Circles indicate a representative bead having red/green fluorescent.
Figure 6:
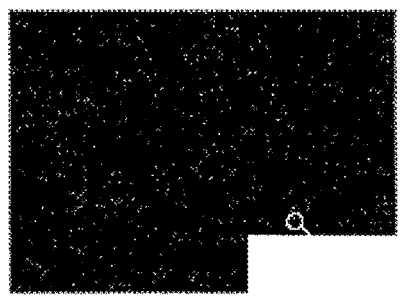
Figure 6:
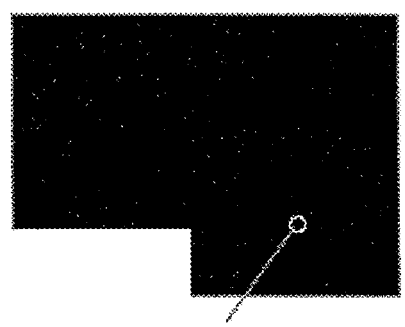

Fluorescently labeled sequencing primers (Read 1 Seq primer; green fluorescent probe and Read 2 Sequencing primer; red fluorescent probe) were annealed to the bead bound ePCR product, such that the beads were visualized using conventional laser illumination and detection technology. See, FIG. 5. Photomicrographs of the fluorescent emission spectra confirmed that oligo A and oligo B were co-localized on the same bead. See, FIG. 6A-C.

We claim:

1. A method, comprising:
   a) providing:
      i) a first forked end adapter comprising a first duplex DNA sequence, wherein said first duplex DNA sequence comprises a first nucleic acid sequence ligated to a first primer sequence and a second nucleic acid sequence ligated to a second primer binding sequence;
      ii) a second forked end adapter comprising a second duplex DNA sequence, wherein said second duplex DNA sequence comprises a third nucleic acid sequence ligated to a third primer sequence and a fourth nucleic acid sequence ligated to a fourth primer binding sequence;
      iii) a genomic DNA fragment capable of ligating said first duplex DNA sequence to said second duplex DNA sequence;
      iv) a second primer capable of binding to said second primer binding sequence;
      v) a fourth primer capable of binding to said fourth primer binding sequence; and
      vi) a bead comprising a first primer having the first primer sequence as recited in i) and a third primer having the third primer sequence as recited in ii), wherein said first and third primers are attached to said bead at their 5' ends;
   b) contacting said genomic DNA fragment with said first forked end adapter and said second forked end adapter wherein said genomic DNA fragment ligates between said first duplex sequence and said second duplex sequence, thereby forming a ligated forked adapter primer pair; and
   c) emulsion amplifying said ligated forked adapter primer pair with said bead, said second primer and said fourth primer, thereby co-localizing a first double stranded bead product and a second double stranded bead product on said bead;
   wherein said first primer, second primer, third primer, and fourth primer have distinct, non-complementary sequences and bind to distinct primer binding sequences.

2. The method of claim 1, wherein said method further comprises denaturing said first double stranded bead product and said second double stranded bead product, thereby forming a first single stranded bead product and a second single stranded bead product.

3. The method of claim 2, wherein said method further comprises hybridizing a first sequencing primer to said first single stranded bead product and a second sequencing primer to said second single stranded bead product.

4. The method of claim 3, wherein said method further comprises sequentially sequencing said first single stranded bead product and said second single stranded bead product.

5. The method of claim 4, wherein said sequencing comprises high throughput sequencing.

6. The method of claim 3, wherein said first sequencing primer and said second sequencing primer are high throughput sequencing primers.

\* \* \* \* \*

SEQUENCE LISTING

```
<160> NUMBER OF SEQ ID NOS: 36

<210> SEQ ID NO 1
<211> LENGTH: 8
<212> TYPE: DNA
<213> ORGANISM: Artificial sequence
<220> FEATURE:
<223> OTHER INFORMATION: synthetic

<400> SEQUENCE: 1 ttgagcct                                                                  8

<210> SEQ ID NO 2
<211> LENGTH: 8
<212> TYPE: DNA
<213> ORGANISM: Artificial sequence
<220> FEATURE:
<223> OTHER INFORMATION: synthetic

<400> SEQUENCE: 2 agttgctt                                                                  8
```

```
<210> SEQ ID NO 3
<211> LENGTH: 8
<212> TYPE: DNA
<213> ORGANISM: Artificial sequence
<220> FEATURE:
<223> OTHER INFORMATION: synthetic

<400> SEQUENCE: 3 ccagttag                                                                  8

<210> SEQ ID NO 4
<211> LENGTH: 8
<212> TYPE: DNA
<213> ORGANISM: Artificial sequence
<220> FEATURE:
<223> OTHER INFORMATION: synthetic

<400> SEQUENCE: 4 accaactg                                                                  8

<210> SEQ ID NO 5
<211> LENGTH: 8
<212> TYPE: DNA
<213> ORGANISM: Artificial sequence
<220> FEATURE:
<223> OTHER INFORMATION: synthetic

<400> SEQUENCE: 5 gtataaca                                                                  8

<210> SEQ ID NO 6
<211> LENGTH: 8
<212> TYPE: DNA
<213> ORGANISM: Artificial sequence
<220> FEATURE:
<223> OTHER INFORMATION: synthetic

<400> SEQUENCE: 6 caggagcc                                                                  8

<210> SEQ ID NO 7
<211> LENGTH: 15
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: 5' connection to bead

<400> SEQUENCE: 7
gcctccctcg cgcca                                                         15

<210> SEQ ID NO 8
<211> LENGTH: 15
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: 5' connection to bead

<400> SEQUENCE: 8
gccttgccag cccgc                                                         15
```

```
<210> SEQ ID NO 9
<211> LENGTH: 19
<212> TYPE: DNA
<213> ORGANISM: Artificial sequence
<220> FEATURE:
<223> OTHER INFORMATION: synthetic

<400> SEQUENCE: 9
ggtagagtag ggacgcacc                                                    19

<210> SEQ ID NO 10
<211> LENGTH: 18
<212> TYPE: DNA
<213> ORGANISM: Artificial sequence
<220> FEATURE:
<223> OTHER INFORMATION: synthetic

<400> SEQUENCE: 10
ggatagggga cacacgga                                                     18

<210> SEQ ID NO 11
<211> LENGTH: 16
<212> TYPE: DNA
<213> ORGANISM: Artificial sequence
<220> FEATURE:
<223> OTHER INFORMATION: synthetic

<400> SEQUENCE: 11
tagggacgca cagagg                                                       16

<210> SEQ ID NO 12
<211> LENGTH: 19
<212> TYPE: DNA
<213> ORGANISM: Artificial sequence
<220> FEATURE:
<223> OTHER INFORMATION: synthetic

<400> SEQUENCE: 12
ggacacacgg aaccgtcag                                                    19

<210> SEQ ID NO 13
<211> LENGTH: 27
<212> TYPE: DNA
<213> ORGANISM: Artificial sequence
<220> FEATURE:
<223> OTHER INFORMATION: synthetic

<400> SEQUENCE: 13
gcctccctcg cgccaaccgt cagagtc                                           27

<210> SEQ ID NO 14
<211> LENGTH: 30
<212> TYPE: DNA
<213> ORGANISM: Artificial sequence
<220> FEATURE:
<223> OTHER INFORMATION: synthetic

<400> SEQUENCE: 14 cctatccoct gtgtgccttg gcagtctcag                                        30

<210> SEQ ID NO 15
<211> LENGTH: 30
<212> TYPE: DNA
<213> ORGANISM: Artificial sequence
<220> FEATURE:
<223> OTHER INFORMATION: synthetic
```

<400> SEQUENCE: 15
gactcagcct ctgtgcgtcc ctactctacc                                           30

<210> SEQ ID NO 16
<211> LENGTH: 27
<212> TYPE: DNA
<213> ORGANISM: Artificial sequence
<220> FEATURE:
<223> OTHER INFORMATION: synthetic

<400> SEQUENCE: 16
ctgagtcgga gacgcccgac cgttccg                                              27

<210> SEQ ID NO 17
<211> LENGTH: 30
<212> TYPE: DNA
<213> ORGANISM: Artificial sequence
<220> FEATURE:
<223> OTHER INFORMATION: synthetic

<400> SEQUENCE: 17
gactcagcct ctgtgcgtcc ctactctacc                                           30

<210> SEQ ID NO 18
<211> LENGTH: 27
<212> TYPE: DNA
<213> ORGANISM: Artificial sequence
<220> FEATURE:
<223> OTHER INFORMATION: synthetic

<400> SEQUENCE: 18
gcctccctcg cgccaaccgt cagagct                                              27

<210> SEQ ID NO 19
<211> LENGTH: 30
<212> TYPE: DNA
<213> ORGANISM: Artificial sequence
<220> FEATURE:
<223> OTHER INFORMATION: synthetic

<400> SEQUENCE: 19
ggtagagtag ggacgcacag aggctgagtc                                           30

<210> SEQ ID NO 20
<211> LENGTH: 27
<212> TYPE: DNA
<213> ORGANISM: Artificial sequence
<220> FEATURE:
<223> OTHER INFORMATION: synthetic

<400> SEQUENCE: 20
gactctgacg gttggcgcga gggaggc                                              27

<210> SEQ ID NO 21
<211> LENGTH: 27
<212> TYPE: DNA
<213> ORGANISM: Artificial sequence
<220> FEATURE:
<223> OTHER INFORMATION: synthetic

<400> SEQUENCE: 21
cggaacggtc gggcgtctcc gactcag                                              27

<210> SEQ ID NO 22
<211> LENGTH: 30
<212> TYPE: DNA
<213> ORGANISM: Artificial sequence
<220> FEATURE:
<223> OTHER INFORMATION: synthetic

<400> SEQUENCE: 22
ctgagactgc caaggcacac agggggatagg                                    30

<210> SEQ ID NO 23
<211> LENGTH: 27
<212> TYPE: DNA
<213> ORGANISM: Artificial sequence
<220> FEATURE:
<223> OTHER INFORMATION: synthetic

<400> SEQUENCE: 23
gccttgccag cccgcagagg ctgagtc                                        27

<210> SEQ ID NO 24
<211> LENGTH: 30
<212> TYPE: DNA
<213> ORGANISM: Artificial sequence
<220> FEATURE:
<223> OTHER INFORMATION: synthetic

<400> SEQUENCE: 24
gactctgacg gttccgtgtg tcccctatcc                                     30

<210> SEQ ID NO 25
<211> LENGTH: 27
<212> TYPE: DNA
<213> ORGANISM: Artificial sequence
<220> FEATURE:
<223> OTHER INFORMATION: synthetic

<400> SEQUENCE: 25
gactctgacg gttggcgcga gggaggc                                        27

<210> SEQ ID NO 26
<211> LENGTH: 30
<212> TYPE: DNA
<213> ORGANISM: Artificial sequence
<220> FEATURE:
<223> OTHER INFORMATION: synthetic

<400> SEQUENCE: 26
ggtagagtag ggacgcacag aggctgagtc                                     30

<210> SEQ ID NO 27
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: 5' attachment to bead

<400> SEQUENCE: 27
gcctccctcg cgccaaccgt cagagtc                                        27

<210> SEQ ID NO 28
<211> LENGTH: 30
<212> TYPE: DNA
<213> ORGANISM: Artificial sequence
<220> FEATURE:
<223> OTHER INFORMATION: synthetic

<400> SEQUENCE: 28
gactcagcct ctgtgcgtcc ctactctacc                                    30

<210> SEQ ID NO 29
<211> LENGTH: 27
<212> TYPE: DNA
<213> ORGANISM: Artificial sequence
<220> FEATURE:
<223> OTHER INFORMATION: synthetic

<400> SEQUENCE: 29
gactcagcct ctgcgggctg gcaaggc                                       27

<210> SEQ ID NO 30
<211> LENGTH: 30
<212> TYPE: DNA
<213> ORGANISM: Artificial sequence
<220> FEATURE:
<223> OTHER INFORMATION: synthetic

<400> SEQUENCE: 30 ggataggga cacacggaac cgtcagagtc                                     30

<210> SEQ ID NO 31
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: 5' attachment to bead

<400> SEQUENCE: 31
gccttgccag cccgcagagg ctgagtc                                       27

<210> SEQ ID NO 32
<211> LENGTH: 30
<212> TYPE: DNA
<213> ORGANISM: Artificial sequence
<220> FEATURE:
<223> OTHER INFORMATION: synthetic

<400> SEQUENCE: 32
gactctgacg gttccgtgtg tcccctatcc                                    30

<210> SEQ ID NO 33
<211> LENGTH: 19
<212> TYPE: DNA
<213> ORGANISM: Artificial sequence
<220> FEATURE:
<223> OTHER INFORMATION: synthetic

<400> SEQUENCE: 33
tagggacgca cagaggctg                                                19

```
<210> SEQ ID NO 34
<211> LENGTH: 19
<212> TYPE: DNA
<213> ORGANISM: Artificial sequence
<220> FEATURE:
<223> OTHER INFORMATION: synthetic

<400> SEQUENCE: 34
ggacacacgg aaccgtcag                                                    19

<210> SEQ ID NO 35
<211> LENGTH: 19
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: 5' label

<400> SEQUENCE: 35
tagggacgca cagaggctg                                                    19

<210> SEQ ID NO 36
<211> LENGTH: 19
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: 5' label

<400> SEQUENCE: 36
ggacacacgg aaccgtcag                                                    19
```